US006471949B2

(12) United States Patent
Candau et al.

(10) Patent No.: US 6,471,949 B2
(45) Date of Patent: *Oct. 29, 2002

(54) COMPOSITIONS COMPRISING AT LEAST ONE UV SCREENING AGENT AND AT LEAST ONE FLAVYLIUM SALT WHICH IS UNSUBSTITUTED IN POSITION 3, FOR COLORING THE SKIN, AND USES THEREOF

(75) Inventors: Didier Candau, Bievres; Serge Forestier, Claye Souilly, both of (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/901,724

(22) Filed: Jul. 11, 2001

(65) Prior Publication Data

US 2002/0064507 A1 May 30, 2002

(30) Foreign Application Priority Data

Jul. 12, 2000 (FR) .............................. 00 09117

(51) Int. Cl.$^7$ ............................ A61K 7/42; A61K 7/44; A61K 7/00
(52) U.S. Cl. ............................ 424/59; 424/60; 424/400; 424/401
(58) Field of Search ............................ 424/59, 60, 400, 424/401

(56) References Cited

U.S. PATENT DOCUMENTS

| 4,247,411 | A | 1/1981 | Vanlerberghe et al. |
| 5,166,355 | A | 11/1992 | Leistner et al. |
| 5,237,071 | A | 8/1993 | Leistner et al. |
| 5,695,747 | A | 12/1997 | Forestier et al. |
| 5,795,565 | A | 8/1998 | Eteve et al. |
| 5,955,060 | A | 9/1999 | Hüglin et al. |
| 5,962,452 | A | 10/1999 | Haase et al. |
| 5,976,512 | A | 11/1999 | Huber |
| 6,159,455 | A | 12/2000 | Habeck et al. |
| 6,191,301 | B1 | 2/2001 | Habeck et al. |
| 6,238,649 | B1 | 5/2001 | Habeck et al. |
| 6,241,785 | B1 | 6/2001 | Darmenton et al. |

FOREIGN PATENT DOCUMENTS

| DE | 197 26 184 | 12/1998 |
| DE | 197 55 649 | 7/1999 |
| DE | 198 55 649 | 6/2000 |
| EP | 0 024 731 | 3/1981 |
| EP | 0 517 104 | 12/1992 |
| EP | 0 518 772 | 12/1992 |
| EP | 0 518 773 | 12/1992 |
| EP | 0 570 838 | 11/1993 |
| EP | 0 775 698 | 5/1997 |
| EP | 0 796 851 | 9/1997 |
| EP | 0 863 145 | 9/1998 |
| EP | 0 878 469 | 11/1998 |
| EP | 0 893 119 | 1/1999 |
| EP | 0 933 376 | 8/1999 |
| EP | 0 967 200 | 12/1999 |
| FR | 2 315 991 | 1/1977 |
| FR | 2 416 008 | 8/1979 |
| FR | 2 757 383 | 6/1998 |
| GB | 2 303 549 | 2/1997 |
| WO | WO 93/04665 | 3/1993 |

OTHER PUBLICATIONS

Co-pending Application No. 09/901,725; Attorney Docket No. 05725.0937–00000 Title: Composition Comprising at Least One Self–Tanning Agent Chosen From Monocarbonyl and Polycarbonyl Compounds and a Flavylium Salt Compound Which is Unsubstituted in Position 3, for Coloring the Skin, and Uses Thereof Inventor(s): Didier Candau et al. U.S. Filing Date: Jul. 11, 2001.

Co-pending Application No. 09/901,720; Attorney Docket No. 05725.0941–00000 Title: Compositions for Coloring the Skin Comprising at Least One Flavylium Salt Which is Unsubstituted in Position 3 and at Least One Organomodified Silicone Inventor(s): Didier Candau et al. U.S. Filing Date: Jul. 11, 2001.

Derwent Publications Ltd., London, GB; AN 1999–338248, XP002164085 (CN 1 209 992).

Derwent Publications Ltd, London, GB; AN 1988–195805, XP002164086 (JP 63 135310).

Derwent Publications Ltd., London, GB; AN 1987–099079, XP002164100 (JP 62 048611).

English language Derwent Abstract of DE 197 26 184, Dec. 24, 1998.

English language Derwent Abstract of FR 2 315 991, Jan. 28, 1977.

A. Chardon et al., "Skin Colour Typology and Suntanning Pathways," International Journal of Cosmetic Science, vol. 13, No. 4, pp. 191–208.

David Doig Pratt et al., "A Synthesis of Pyrylium Salts of Anthocyanidin Type. Part II,", Journal of The Chemical Society, vol. CXXIII, 1923, pp. 745–757.

Alexander Robertson et al., "A Synthesis of Pyrylium Salts of Anthocyanidin Type. Part IX. Some Hydroxyflavylium Salts," Journal of The Chemical Society, Jul. 1926, pp. 1951–1959.

(List continued on next page.)

Primary Examiner—Shelly A. Dodson
(74) Attorney, Agent, or Firm—Finnegan, Henderson, Farabow, Garrett & Dunner, LLP

(57) ABSTRACT

A cosmetic and/or dermatological composition intended for artificially coloring the skin, which comprises, in, for example, a cosmetically acceptable support, at least one compound capable of screening out ultraviolet radiation and at least one flavylium salt compound which is unsubstituted in position 3, and which is substituted with at least one radical chosen from hydroxyl and alkoxy radicals, wherein the at least one flavylium salt compound may be obtained, for example, in a manner chosen from synthetically, from a plant extract containing it, and from an enriched plant extract containing it. The invention also relates to the uses of these compositions for coloring the skin.

44 Claims, No Drawings

OTHER PUBLICATIONS

Alexander Robertson et al., "A Synthesis of Pyrylium Salts of Anthocyanidin Type. Part XIV," Journal of The Chemical Society, 1927, pp. 2196–2206.

Alexander Robertson et al. "Snythesis of Pyrylium Salts of Anthocyanidin Type. Part XV. The Synthesis of Cyanidin Chloride by Means of O–Benzoylphloroglucinaldehyde," Journal of The Chemical Society, 1928, pp. 1526–1532.

J.G. Sweeny et al., "Synthesis of Anthocyanidins—The Oxidative Generation of Flavylium Cations Using Benzoquinones," Tetrahedron, vol. 33, 1977, pp. 2923–2926.

Janet C. Bell et al., "Experiments on the Synthesis of Anthocyanins. Part XX. Synthesis of Malvidin 3–Galactoside and its Probable Occurrence as a Natural Anthocyanin," Journal of The Chemical Society, 1934, pp. 813–818.

A.D. Bangham et al., "Diffusion of Univalent Ions Across the Lamellae of Swollen Phospholipids," Journal of Molecular Biology, vol. 13, No. 1, Aug. 1965, pp. 238–252.

COMPOSITIONS COMPRISING AT LEAST ONE UV SCREENING AGENT AND AT LEAST ONE FLAVYLIUM SALT WHICH IS UNSUBSTITUTED IN POSITION 3, FOR COLORING THE SKIN, AND USES THEREOF

The present invention relates to cosmetic and/or dermatological compositions for artificially coloring the skin, which comprise, in a cosmetically acceptable support, at least one compound capable of screening out ultraviolet radiation and at least one flavylium salt compound which is unsubstituted in position 3, and which is substituted with at least one radical chosen from hydroxyl and alkoxy radicals, wherein the at least one flavylium salt compound may be obtained, for example, in a manner chosen from synthetically, from a plant extract containing it, and from an enriched plant extract containing it.

The invention also relates to the use of these compositions for coloring the skin.

Nowadays, it is important to look healthy, and a tanned skin is always a sign of good health. However, a natural tan may not always be desirable since it requires long exposure to UV radiation, for example, to UV-A radiation which causes tanning of the skin. UV-A radiation is also liable to induce an adverse change of the skin, for example, in the case of sensitive skin and of skin which is continually exposed to solar radiation. It is thus desirable to find an alternative to a natural tan which may be compatible with the requirements of such skin types.

Most of the cosmetic products intended for artificially tanning the skin are based on monocarbonyl and polycarbonyl compounds which, by interacting with the amino acids in the skin, allow the formation of colored products.

To this end, it is known that dihydroxyacetone ("DHA"), is a product which is commonly used in cosmetics as an agent for artificially tanning the skin. When applied to the skin, for example, to the face, it gives a tanning or bronzing effect which may be similar in appearance to that which may result from prolonged exposure to sunlight (a natural tan) or under a UV lamp.

One drawback of DHA can be the length of time the coloration takes to develop. Specifically, several hours (3 to 5 hours in general) may be required for the coloration to be revealed.

Furthermore, DHA can have an annoying tendency, which is more or less pronounced depending on the nature of the medium in which it is formulated, to degrade over time. This degradation is generally reflected in the long run by an undesirable yellowing of the compositions containing it. The result of such a phenomenon is that the activity of DHA, such as its ability to color the skin, may be reduced when these compositions are applied to the skin. Thus, the intensity of the coloration and the staying power of the coloration over time that are obtained on the skin may be unsatisfactory.

Thus, efforts are still under way to find novel compounds and novel compositions which can give the skin an artificial coloration, for example, close to that of a natural tan in at least one of a simple, effective, fast and risk-free manner. It is also sought to obtain a coloration which is at least one of more homogeneous and longer-lasting.

Anthocyanin colorants have been known for a long time as pharmaceutical and food colorants. These anthocyans may be present in nature in the form of heterosides known as anthocyanosides and genins, known as anthocyanidines. These anthocyans may be phenyl-2-benzopyrylium derivatives and flavylium derivatives and may be present, for example, in plants in the form of salts. Anthocyans may be red-, violet- and blue-colored compounds which generally color flowers, fruit and occasionally leaves. The color observed may depend both on the structure of the predominant genin and on the conditions of the medium in which the anthocyanin colorants are present.

Now, after considerable research conducted in the field of artificial coloring of the skin, the Inventorss have discovered that the combination of at least one agent for screening UV radiation chosen from organic and mineral agents and of at least one flavylium salt compound unsubstituted in position 3, may, for example, immediately give the skin, after the product has been applied thereto, an artificial coloration, for example, close to that of a natural tan. Furthermore, the said combination may make it possible to obtain a shade which is at least one of more uniform and longer-lasting than a self-tanning agent of the carbonyl type, such as DHA.

One subject of the present invention is thus novel cosmetic and/or dermatological compositions for giving the skin an artificial coloration, for example, close to that of a natural tan, comprising, in a cosmetically acceptable support, at least one agent for screening out UV radiation chosen from organic and mineral agents and at least one flavylium salt compound which is unsubstituted in position 3, and which is substituted with at least one radical chosen from hydroxyl and alkoxy radicals, wherein the at least one flavylium salt compound may be, for example, obtained in a manner chosen from synthetically, from a plant extract containing it, and from an enriched plant extract containing it.

Another subject of the present invention is the novel use of the combination of at least one agent for screening out UV radiation chosen from organic and mineral agents and of at least one flavylium salt compound which is unsubstituted in position 3, and which is substituted with at least one radical chosen from hydroxyl and alkoxy radicals, wherein the at least one flavylium salt compound may be obtained, for example, in a manner chosen from synthetically, from a plant extract containing it, and from an enriched plant extract containing it, in cosmetic and/or dermatological compositions, with the aim of giving the skin an artificial coloration, for example, close to that of a natural tan.

A subject of the present invention is also a process for giving the skin an artificial coloration, for example, close to that of a natural tan, comprising applying to the skin an effective amount of the combination of at least one agent for screening out UV radiation chosen from organic and mineral agents and of at least one flavylium salt compound which is unsubstituted in position 3, and which is substituted with at least one radical chosen from hydroxyl and alkoxy radicals, wherein the at least one flavylium salt compound may be obtained, for example, in a manner chosen from synthetically, from a plant extract containing it, and from an enriched plant extract containing it.

The compositions and uses in accordance with the invention may make it possible to obtain an artificial coloration, for example, close to that of a natural tan, in a very short space of time. Thus, an immediate coloration may be obtained, which may allow at least one of the following properties: visualization of the application, and better homogeneity in the spreading of the composition on the skin and thus of the resulting coloration. Furthermore, the artificial coloration obtained on the skin according to the invention may be extremely close to that of a natural tan.

For the purposes of the present invention, the expression "composition intended for artificially coloring the skin" will be understood to mean a formulation with a particular affinity for the skin which allows it to give the skin a long-lasting coloration, which may be at least one of non-covering (that is to say which does not have a tendency to opacify the skin), not removed with at least one of water and solvents, and able to withstand both rubbing and washing with a solution containing surfactants. Such a long-lasting coloration may thus be distinguished from the superficial and transient coloration provided, for example, by a make-up product.

At least one other characteristic, aspect and advantage of the present invention may become apparent on reading the detailed description which follows.

The compositions in accordance with the present invention can, for example, generally lead, 30 minutes after application to a fair skin at a rate of 2 mg/cm², to a darkening characterized in the (L*, a*, b*) colorimetric measuring system by a ΔL* ranging from −0.5 to −20. For example, ΔL* may range from −0.5 to −15.

The compositions in accordance with the present invention can, for example, give, 30 minutes after application to the skin at a rate of 2 mg/cm², a coloration on a fair skin, defined in the (L*, a*, b*) calorimetric measuring system by a ratio Δa*/Δb*, ranging from 0.5:1 to 3:1, for example, ranging from 0.8:1 to 2:1.

According to the present invention, the term "fair skin" should be understood to indicate an untanned skin whose colorimetric characteristics may be defined by its ITA angle as defined in the publication by A. Chardon et al., "Skin Color Typology and Suntanning Pathways" presented at the 16 th IFSCC congress, Oct. 8–10, 1990, New York, and in Int. *J. Cosm. Sci.* 13 191–208 (1991), the disclosures of both references relating to such calorimetric characteristics are herein incorporated by reference. The fair skin as defined in this classification may have an ITA angle of from 35 to 55.

In the (L,* a,* b*) colorimetric measuring system: L* is luminance or clarity, a* is the red-green axis (−a*=green,+a*=red) and b* is the yellow-blue axis (−b*=blue,+b*=yellow). Thus, a* and b* express the shade of the skin.

ΔL* reflects the darkening of the color: the more negative the ΔL*, the darker the color becomes, with:

ΔL*=L* uncolored skin−L* colored skin

The ratio Δa*/Δb* reflects the red/yellow balance and thus the shade, with:

Δa*=a* uncolored skin−a* colored skin

Δb*=b* uncolored skin−b* colored skin

The at least one flavylium salt compounds which may be unsubstituted in position 3 include, for example, those corresponding to formula (I) below:

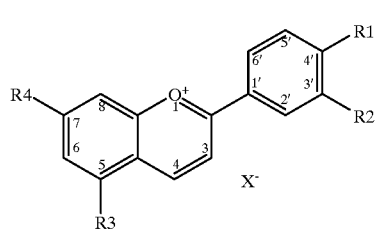

(I)

wherein:
R₁ is chosen from OH and linear and branched, saturated and unsaturated (C₁–C₈) alkoxy radicals,
R₂, R₃ and R₄, which may be identical or different, are chosen from H and R₁, it being understood that, for example, in one embodiment of the invention, at least one of the radicals R₁ to R₄ is OH,
X⁻ is chosen from organic ions and mineral anions. For example, X⁻ can be chosen from anions derived from mineral acid derivatives, and can be chosen from, for example, halides, such as, for example, bromide and chloride. As another example, X⁻ can be chosen from an anion derived from an organic acid, and can be chosen from, for example, acetate, borate, citrate, tartrate, lactate, bisulphate, sulphate, and phosphate.

The at least one flavylium salt compounds of formula (I) may be, according to the present invention, chosen from the group for which, in formula (I), R₁ is chosen from OH and OCH₃.

Among these, mention may be made, for example, of the chlorides of the following compounds:

4',5,7-trihydroxyflavylium, commonly known as "apigeninidine chloride",

3',4',7-trihydroxyflavylium,

4'-hydroxyflavylium,

4',7-dihydroxyflavylium,

3',4'-dihydroxyflavylium,

3',4'-dihydroxy-7-methoxyflavylium,

3',4',5,7-tetrahydroxyflavylium,

3',4',5',5,7-pentahydroxyflavylium.

For example, the at least one flavylium salt compound may be chosen from at least one of apigeninidine chloride (4',5,7-trihydroxyflavylium chloride) and 3',4',7-trihydroxyflavylium chloride. These compounds can be prepared in pure form, i.e., in a form at least 90% pure According to certain embodiments, the present invention comprises using apigeninidine chloride in the form of, or derived from, a plant extract, which can be readily prepared by extraction and isolation from leaves of *Sorghum caudatum* according to, for example, at least one of the processes disclosed in patents CN 1,064,284A and CN 1,035,512C, the disclosures in both patents directed to said extraction and/or isolation are hereby incorporated by reference, and variants of these processes.

According to certain embodiments, the at least one flavylium salt compound may be chosen from those extracted from at least one of the stems, seeds, and leaves of *Sorghum bicolour*; the petals of Gesneria fulgens; and at least one of the species *Blechum procerum* and Sorghum in combination with *Colletotrichum graminicola*.

According to certain embodiments, the present invention comprises using an extract from the leaves of Sorghum bicolour, which can be obtained by an aqueous-alcoholic extraction in acidic medium at an extraction temperature ranging from 30 to 40° C. with a ratio of the volume of solvent to the mass of *Sorghum bicolor* leaves ranging from 10:1 to 30:1. The Sorghum plant extract can have an approximate titre ranging from 0.05% to 50% by weight of apigeninidine chloride.

The at least one flavylium salt compound which is unsubstituted in position 3 and which is substituted with at least one radical chosen from hydroxyl and alkoxy radicals, may be readily and/or cheaply obtained by synthesis, for example, by the well-known method of R. Robinson and D. Pratt, *J. Chem. Soc.* 745 (1923), the disclosure of which directed to said synthesis is hereby incorporated by reference. The method comprises condensing at least one of an ortho-hydroxybenzaldehyde and a substituted ortho-hydroxybenzaldehyde with at least one of an acetophenone and a substituted acetophenone to yield, by selecting the substituents, a desired at least one flavylium salt compound, corresponding to formula (I).

Taking apigeninidine chloride (4',5,7-trihydroxyflavylium chloride) as an example, the synthetic scheme (i) may be as follows:

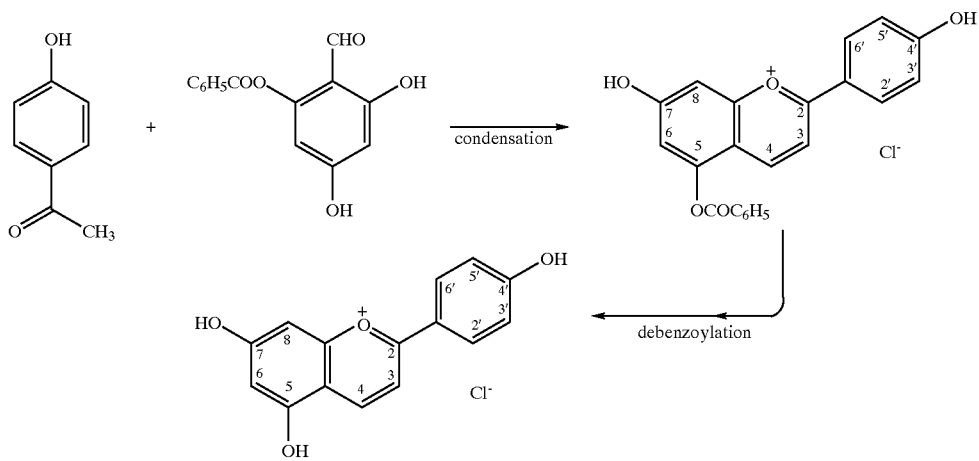

Taking 3',4',7-trihydroxyflavylium chloride as an example, the synthetic scheme (ii) may be as follows:

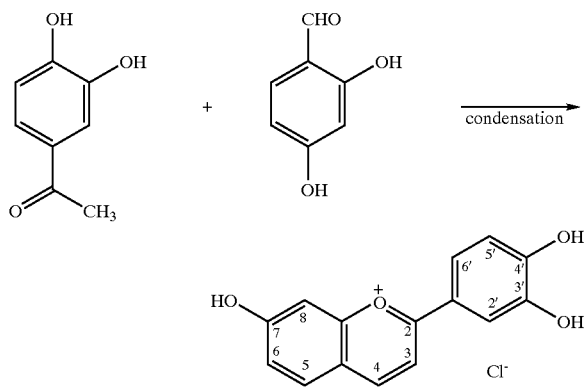

A variety of synthetic routes, for example those that are well known in the field, may be used to lead to apigeninidine.

One method for preparing apigeninidine comprises, for example, in a first step, preparing trimethylapigeninidine by condensing commercial 4,6-dimethoxy-2-hydroxybenzaldehyde with commercial 4-methoxyacetophenone in an anhydrous ether medium at 0° C., and saturating with anhydrous HCl, to yield, after filtration, an orange-red precipitate of trimethylapigeninidine. In a second step, the trimethylapigeninidine obtained in the preceding step is hydrolyzed to apigeninidine chloride, the reaction being carried out in a medium of HI and phenol and AgCl dissolved in methanol. Such a synthetic method is disclosed for example, by R. Robinson and A. Robertson in *J. Chem. Soc.* 1951 (1926) and 2196 (1927), the disclosure of which directed to said synthesis is incorporated herein by reference.

Another method, for example, for preparing apigeninidine comprises condensing 2,4,6-trihydroxybenzaldehyde with 4-hydroxyacetophenone at 0° C. in an anhydrous solvent medium, for example ethyl acetate, and saturating with anhydrous HCl, to yield apigeninidine chloride. Such a method is disclosed, for example, by R. Robinson and A. Robertson in *J. Chem. Soc.* 1528 (1928), the disclosure of which directed to said synthesis is hereby incorporated by reference.

Another method, for example, for preparing apigeninidine chloride comprises reducing at least one of a flavone, naringenin, and triacetyl derivatives thereof, with $NaBH_4$, and then oxidizing the product obtained with chloranil (tetrachloro-1,4-benzoquinone). The method is disclosed, for example, by J. G. Sweeny and G. A. Iacobucci in the review Tetrahedron 33 2923–2927 (1977), the disclosure of which directed to said synthesis is hereby incorporated by reference.

As a further example, use may be made of a method comprising condensing 2,4-dihydroxy-6-benzoyloxybenzaldehyde with 4-hydroxyacetophenone at 0° C. in an anhydrous ethyl acetate medium, saturating with anhydrous HCl and then debenzoylating the product obtained with sodium hydroxide, to yield apigeninidine chloride in high yield, according to scheme (i) described above. The method is disclosed, for example, by R. Robinson and J. C. Bell in J. Chem. Soc. 813 (1934), the disclosure of which directed to said synthesis is hereby incorporated by reference.

The concentration of the at least one flavylium salt compound as described according to the present invention may generally range, for example, from 0.0001% to 10%, such as, for further example, from 0.001% to 5%, by weight relative to the total weight of the composition.

The composition of the present invention may contain at least one agent for screening out ultraviolet radiation, wherein said at least one agent may be chosen from organic UV screening agents and mineral agents.

The organic UV screening agents in accordance with the invention may be chosen from water-soluble agents, liposoluble agents and agents which are insoluble in usual cosmetic solvents. These agents may be chosen from, for example, anthranilates; cinnamic derivatives; dibenzoylmethane derivatives, salicylic derivatives; camphor derivatives, triazine derivatives such as those disclosed in patent applications U.S. patent application Nos. 4,367,390, EP 863145, EP 517104, EP 570838, EP 796851, EP 775698, EP 878469 and EP 933376, the disclosures of each of which relating to UV screening agents are herein incorporated by reference; benzophenone derivatives; β,β'-diphenylacrylate derivatives, benzotriazole derivatives, benzimidazole derivatives; imidazolines; bisbenzazolyl derivatives such as those disclosed in patents EP 669 323 and U.S. Pat. No. 2,463,264, the disclosures of both of which are herein incorporated by reference; p-aminobenzoic acid (PABA) derivatives; methylene bis(hydroxyphenylbenzotriazole) derivatives such as those disclosed in patent applications U.S. Pat. No. 5,237,071, U.S. Pat. No. 5,166,355, GB 2 303

549, DE 19 726 184 and EP 893 119, the disclosures of each of which are herein incorporated by reference; screening polymers and screening silicones such as those disclosed in patent application WO 93/04665, the disclosure of which is herein incorporated by reference; dimers derived from α-alkylstyrene, such as those disclosed in patent application DE 19 855 649, the disclosure of which is herein incorporated by reference; 4,4-diarylbutadiene derivatives such as those disclosed in patent applications EP 0 967 200 and DE 19 755 649, the disclosures of both of which are herein incorporated by reference.

Examples of the at least one organic screening agent, denoted hereinabove by their INCI name, include:

Para-aminobenzoic acid derivatives

PABA,

Ethyl PABA,

Ethyl dihydroxypropyl PABA,

Ethyihexyl dimethyl PABA sold, for example, under the name "Escalol 507" by ISP, Glyceryl PABA, PEG-25 PABA sold under the name "Uvinul P25" by BASF, Salicylic derivatives Homosalate sold under the name "Eusolex HMS" by Rona/EM Industries, Ethyl hexyl salicylate sold under the name "Neo Heliopan OS" by Haarmann and Reimer, Dipropylene glycol salicylate sold under the name "Dipsal" by Scher, TEA salicylate sold under the name "Neo Heliopan TS" by Haarmann and Reimer, Dibenzoylmethane derivatives Butyl methoxydibenzoylmethane sold, for example,under the trade name "Parsol 1789" by Hoffmann-La Roche, Isopropyidibenzoylmethane, Cinnamic derivatives Ethyihexyl methoxycinnamate sold, for example,under the name "Parsol MCX" by Hoffmann La Roche, Isoproyl methoxycinnamate, Isoamyl methoxy cinnamate sold under the trade name "Neo Heliopan E 1000" by Haarmann and Reimer, Cinoxate, DEA methoxycinnamate, Diisopropyl methylcinnamate, Glyceryl ethylhexanoate dimethoxycinnamate β,β'-diphenylacrylate derivatives Octocrylene sold, for example, under the trade name "Uvinul N539" by BASF, Etocrylene, sold, for example, under the trade name "Uvinul N35" by BASF, Benzophenone derivatives Benzophenone-1 sold under the trade name "Uvinul 400" by BAS F, Benzophenone-2 sold under the trade name "Uvinul D50" by BAS F, Benzophenone-3 or Oxybenzone, sold under the trade name "Uvinul M40" by BASF, Benzophenone-4 sold under the trade name "Uvinul MS40" by BAS F, Benzophenone-5

Benzophenone-6 sold under the trade name "Helisorb 11" by Norquay

Benzophenone-8 sold under the trade name "Spectra-Sorb UV-24" by American Cyanamid Benzophenone-9 sold under the trade name "Uvinul DS-49" by BASF, Benzophenone-12

Benzylidene camphor derivatives

3-Benzylidene camphor manufactured under the name "Mexoryl SD" by Chimex,

4-Methylbenzylidene camphor sold under the name "Eusolex 6300" by Merck,

Benzylidenecamphorsulphonic acid manufactured under the name "Mexoryl SL" by Chimex, Camphor benzalkonium methosulphate manufactured under the name "Mexoryl SO" by Chimex, Terephthalylidenedicamphorsulphonic acid manufactured under the name "Mexoryl SX" by Chimex, Polyacrylamidomethylbenzylidenecamphor manufactured under the name "Mexoryl SW" by Chimex, Phenylbenzimidazole derivatives Phenylbenzimidazolesulphonic acid sold, for example, under the trade name "Eusolex 232" by Merck, Benzimidazilate sold under the trade name "Neo Heliopan AP" by Haarmann and Reimer, Triazine derivatives Anisotriazine sold under the trade name "Tinosorb S" by Ciba-Geigy, Ethylhexyltriazone sold, for example, under the trade name "Uvinul TI 50" by BASF, Diethylhexylbutamidotriazone sold under the trade name "Uvasorb HEB" by Sigma 3V, Phenylbenzotriazole derivatives Drometrizole trisiloxane sold under the name "Silatrizole" by Rhodia Chimie, Methylenebis(benzotriazolyl)tetramethylbutylphenol, sold in solid form under the trade name "Mixxim BB/100" by Fairmount Chemical and in micronized form at an aqueous dispersion, under the trade name "Tinosorb M" by Ciba Specialty Chemicals, Anthranilate derivatives Menthyl anthranilate sold under the trade name "Neo Heliopan MA" by Haarmann and Reimer, Imidazoline derivatives Ethylhexyldimethoxybenzylidenedioxoimidazoline propionate, Benzylmalonate derivatives Polyorganosiloxane containing benzalmalonate functions, sold under the trade name "Parsol SLX" by Hoffmann La Roche.

For example, the at least one organic UV screening agent may be chosen from the following compounds:

Ethylhexyl salicylate,

Butyl methoxydibenzoylmethane,

Ethylhexyl methoxycinnamate,

Octocrylene,

Phenylbenzimidazolesulphonic acid,

Terephthalylidenedicamphorsulphonic acid,

Benzophenone-3,

Benzophenone-4,

Benzophenone-5,

4-Methylbenzylidenecamphor,

Benzimidazilate,

Anisotriazine,

Ethylhexyltriazone,

Diethylhexylbutamidotriazone,

Methylenebis(benzotriazolyl)tetramethylbutylphenol, and

Drometrizole trisiloxane.

The mineral screening agents are generally chosen from pigments and nanopigments (average size of the primary particles: generally range from 5 nm to 100 nm, for example, such as from 10 nm to 50 nm) of coated and uncoated metal oxides, such as, for example, nanopigments of titanium oxide (amorphous form, crystallized in rutile form, and crystallized in anatase form), of iron oxide, of zinc oxide, of zirconium oxide and of cerium oxide, which are all UV stabilizers that are well known per se. Conventional coating agents may be, for example, chosen from alumina and aluminium stearate. Such coated and uncoated metal oxide nanopigments are disclosed, for example, in patent applications EP-A-0 518 772 and EP-A-0 518 773, the disclosures of which related to said nanopigments are herein incorporated by reference.

The radiation-screening agents may generally be present in the compositions according to the invention in proportions generally ranging from, for example, 0.1% to 20% by weight relative to the total weight of the composition, for further example, such as from 0.2% to 15% by weight relative to the total weight of the composition.

The compositions in accordance with the present invention may also comprise at least one conventional cosmetic adjuvant chosen, for example, from fatty substances, organic solvents, ionic and nonionic thickeners, softeners, antioxidants, free-radical scavengers, opacifiers, stabilizers, emollients, silicones, α-hydroxy acids, antifoams, moisturizers, vitamins, fragrances, preserving agents, surfactants, fillers, polymers, propellants, acidifying and basifying agents, colorants and any other ingredient usually used in cosmetics and dermatology, such as, for example, in manufacturing antisun compositions in the form of emulsions.

At least one fatty substance may be chosen from oils and waxes. The term "oil" means a compound which is liquid at room temperature. The term "wax" means a compound which is solid or substantially solid at room temperature and whose melting point is generally greater than 35° C.

Examples of oils include mineral oils (paraffin); plant oils (sweet almond oil, macadamia oil, blackcurrent seed oil, jojoba oil); synthetic oils such as perhydrosqualene, fatty alcohols, fatty acids and fatty esters (such as the $C_{12}$–$C_{15}$ alkyl benzoate sold under the trade name "Finsolv TN" by the company Finetex, octyl palmitate, isopropyl lanolate, triglycerides including those of capric/caprylic acid), oxyethylenated and oxypropylenated fatty esters and ethers; silicone oils (cyclomethicone and polydimethylsiloxanes ("PDMSs")) and fluoro oils, and polyalkylenes.

Examples of waxy compounds include paraffin, carnauba wax, beeswax and hydrogenated castor oil.

Examples of organic solvents include lower alcohols and polyols.

According to one embodiment, the compositions according to the invention may contain at least 5% by weight, relative to the weight of the composition, of at least one polyhydroxylated solvent. These solvents may be chosen from glycols and glycol ethers, for instance ethylene glycol, propylene glycol, butylene glycol, dipropylene glycol and diethylene glycol. For example, the compositions according to the invention may contain a mixture of at least three different polyhydroxylated solvents, such as, for example, a mixture comprising propylene glycol, butylene glycol and dipropylene glycol.

The thickeners may be chosen, for example, from crosslinked polyacrylic acids, modified guar gums, unmodified guar gums and celluloses, such as hydroxyprolyl guar gum, methylhydroxyethylcellulose and hydroxypropylmethylcellulose.

Needless to say, a person skilled in the art will take care to select the optional additional compound(s) mentioned above and the amounts thereof such that at least one advantageous property that can be associated with the combination in accordance with the invention is not, or is not substantially, adversely affected by the addition(s) envisaged.

The composition according to the invention may be prepared according to the techniques that are well known to those skilled in the art, for example, such as those intended for preparing oil-in-water and water-in-oil emulsions.

The compositions of the present invention may be, for example, in at least one form chosen from simple and complex (O/W, W/O, O/W/O or W/O/W) emulsions (such as creams and milks), gels, cream-gels, lotions, powders, solid tubes, aerosols, mousses and sprays.

When the composition of the present invention comprises an emulsion, the aqueous phase of this emulsion may comprise a nonionic vesicular dispersion prepared according to known processes, such as is disclosed in Bangham, Standish and Watkins, J. Mol. Biol. 13, 238 (1965), FR 2 315 991 and FR 2 416 008, the disclosures of each of which relating to such emulsions are herein incorporated by reference.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Non-limiting examples illustrating the invention will now be given.

EXAMPLE 1

An extract of Sorghum bicolor with a titre of 20–30% of apigeninidine chloride was prepared according to the following preparation process:

An extract from the leaves of Sorghum bicolor was obtained by aqueous-alcoholic (95° ethanol) extraction in acidic medium (0.2% HCl) at an extraction temperature of 35° C. with a ratio of the volume of solvent to the mass of Sorghum bicolor leaves of 15. The Sorghum plant extract was oven-dried for 24 h at 40° C. and screened at 200 μm.

The yield for this extraction was 22.42% colorant matter.

The titre for the extract thus obtained was 21% by weight of apigeninidine chloride.

This example was intended to show the intensity of the coloration obtained with an extract of Sorghum bicolor associated with a UV screening agent in accordance with the present invention, and also the speed with which this coloration develops compared with a composition containing DHA alone as skin-coloring agent.

The inventors prepared the following compositions (the amounts are expressed as percentages by weight relative to the total weight of the composition):

| Composition A (not according to the invention): | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Dihydroxyacetone (DHA) | 4 g |
| Sodium chloride | 2 g |
| Propylene glycol | 23 g |
| Butylene glycol | 5 g |
| Dipropylene glycol | 10 g |
| Demineralized water | 32.649 g |
| Trisodium citrate | 0.542 g |
| Citric acid | 0.209 g |

| Composition B (invention): | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Demineralized water | 35.659 g |
| Benzene-1,4-bis(3-methylidene-10-camphorsulphonic acid) | 0.5 g |
| Sodium chloride | 2 g |
| Propylene glycol | 23 g |
| Butylene glycol | 5 g |
| Dipropylene glycol | 10 g |
| Extract of Sorghum bicolour as prepared above | 0.5 g |
| Trisodium citrate | 0.535 g |
| Citric acid | 0.206 g |

Evaluation protocol

Compositions A and B were applied at a rate of 2 mg/cm² to an area of 7×4.5 cm² delimited on the back of six volunteers whose skin color, characterized by the ITA angle, was between 35 and 55.

The five series of calorimetric measurements below were carried out using a Minolta CR-300 calorimeter:

1) before applying the composition, 2) 30 minutes after the application, 3) 2 hours after application, 4) 4 hours after application.

The results were expressed in the (L*, a*, b*) system in which L* represented the luminance, a* represented the red-green axis (−a*=green, +a*=red) and b* represented the yellow-blue axis (−b*=blue, +b*=yellow). Thus, a* and b* expressed the shade of the skin.

To evaluate the intensity of the coloration, the important value was the $\Delta L^*$ which reflected the darkening of the color: the more negative the $\Delta L^*$, the more the color was darkened, with:

$$\Delta L^* = L^* \text{ uncolored skin} - L^* \text{ colored skin}$$

The results obtained were collated in Table (I) below:

TABLE (I)

| | Composition A (comparative) $\Delta L^*$ | Composition B (invention) $\Delta L^*$ |
|---|---|---|
| 30 minutes | −0.4 | −8.2 |
| 2 hours | −1.1 | −7 |
| 4 hours | −2.5 | −6.7 |

It was thus found that 30 minutes after application, composition A, which contained DHA as a skin-coloring agent, gave the skin only a very faint coloration, since the DHA had not yet had the time to act ($\Delta L^* = -0.4$). On the other hand, composition B according to the invention had already given the skin a significant coloration ($\Delta L^* = -8.2$).

What is claimed is:

1. A cosmetic and/or dermatological composition for giving the skin an artificial coloration comprising,
   at least one agent chosen from organic and mineral agents for screening out ultraviolet radiation, and
   at least one flavylium salt compound which is unsubstituted in position 3 and which is substituted with at least one radical chosen from hydroxyl and alkoxy radicals.

2. The composition according to claim 1, wherein the artificial coloration is close to that of a natural tan.

3. The composition according to claim 1, further comprising a cosmetically acceptable support.

4. The composition according to claim 1, wherein the composition produces, 30 minutes after application to a fair skin at a rate of 2 mg/cm², a darkening of color of the skin wherein $\Delta L^*$ ranges from −0.5 to −20.

5. The composition according to claim 4, wherein the $\Delta L^*$ ranges from −0.5 to −15.

6. The composition according to claim 1, wherein the composition produces, 30 minutes after application to a fair skin at a rate of 2 mg/cm², a coloration defined by a ratio $\Delta a^*/\Delta b^*$ ranging from 0.5:1 to 3:1.

7. The composition according to claim 6, wherein the ratio $\Delta a^*/\Delta b^*$ ranges from 0.8:1 to 2:1.

8. The composition according to claim 1, wherein the at least one flavylium salt compound corresponds to formula (I) below:

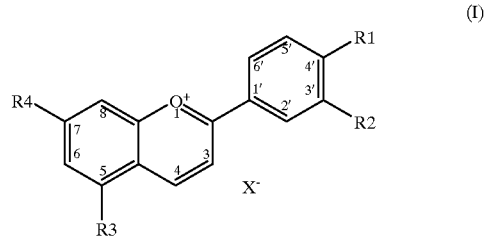

wherein:
   $R_1$ is chosen from an OH radical and linear and branched, saturated and unsaturated ($C_1$–$C_8$) alkoxy radicals,
   $R_2$, $R_3$ and $R_4$, which may be identical or different, are chosen from H and $R_1$, it being understood that at least one of the radicals $R_1$ to $R_4$ is an OH radical,
   $X^-$ is chosen from organic anions and a mineral anions.

9. The composition according to claim 8, wherein $X^-$ is chosen from halides and organic acid derivatives.

10. The composition according to claim 8, wherein $R_1$ is chosen from an OH radical and $OCH_3$.

11. The composition according to claim 8, wherein the at least one flavylium salt compound corresponding to formula (I) is chosen from a salt of:
   4',5,7-trihydroxyflavylium,
   3',4',7-trihydroxyflavylium,
   4'-hydroxyflavylium,
   4',7-dihydroxyflavylium,
   3',4'-dihydroxyflavylium,
   3',4'-dihydroxy-7-methoxyflavylium,
   3',4',5,7-tetrahydroxyflavylium, and 3',4',5',5,7-pentahydroxyflavylium.

12. The composition according to claim 11, wherein the at least one flavylium salt compound is 4',5,7-trihydroxyflavylium chloride.

13. The composition according to claim 12, wherein the 4',5,7-trihydroxyflavylium chloride is synthetically formed.

14. The composition according to claim 12, wherein the 4',5,7-trihydroxyflavylium chloride is in the form of a plant extract.

15. The composition according to claim 14, wherein the plant extract is a plant extract obtained from at least one of leaves of Sorghum caudatum; stems, seeds, and leaves of *Sorghum bicolour*, petals of *Gesneria fulgens;* and at least one species chosen from *Blechumprocerum* and Sorghum in combination with Colletotrichumgraminicola.

16. The composition according to claim 14, wherein the plant extract is an extract of *Sorghum bicolour* obtained by an acidic aqueous-alcoholic extraction at an extraction temperature ranging from 30° C. to 40° C. with a ratio of the volume of solvent to the mass of *Sorghum bicolour* leaves ranging from 10:1 to 30:1.

17. The composition according to claim 16, wherein the extract of *Sorghum bicolour* has a titre of from 0.05% to 50% by weight 4',5,7-trihydroxyflavylium chloride.

18. The composition according to claim 1, wherein a concentration of the at least one flavylium salt compound ranges from 0.0001% to 10% by weight relative to the total weight of the composition.

19. The composition according to claim 18, wherein a concentration of the at least one flavylium salt compound ranges from 0.001% to 5% by weight relative to the total weight of the composition.

20. The composition according to claim 1, wherein the organic agent for screening out UV radiation is chosen from water-soluble agents, liposoluble agents and agents which are insoluble in usual cosmetic solvents.

21. The composition according to claim 20, wherein the organic agent for screening out UV radiation is chosen from anthranilates; cinnamic derivatives; dibenzoylmethane derivatives; salicylic derivatives; camphor derivatives; triazine derivatives; benzophenone derivatives; β,β'-diphenylacrylate derivatives, benzotriazole derivatives, benzimidazole derivatives; imidazolines; bis-benzazolyl derivatives; p-aminobenzoic acid (PABA) derivatives; methylenebis(hydroxyphenylbenzotriazole) derivatives; screening polymers and screening silicones; dimers derived from α-alkylstyrene; and 4,4-diarylbutadiene derivatives.

22. The composition according to claim 21, wherein the organic agent for screening out UV radiation is chosen from:
    Ethylhexyl salicylate,
    Butylmethoxydibenzoylmethane,
    thyihexyl methoxycinnamate,
    Octocrylene,
    Phenylbenzimidazolesulphonic acid,
    Terephthalylidene dicamphorsulphonic acid,
    Benzophenone-3,
    Benzophenone-4,
    Benzophenone-5,
    4-Methylbenzylidenecamphor,
    Benzimidazilate,
    Anisotriazine,
    Ethylhexyltriazone,
    Diethylhexylbutamidotriazone,
    Methylenebis(benzotriazolyl)tetramethylbutylphenol, and
    Drometrizole trisiloxane.

23. The composition according to claim 1, wherein the said at least one agent for screening out UV radiation is a mineral agent chosen from pigments and nanopigments.

24. The composition according to claim 23, wherein said pigments and nanopigments are chosen from coated and uncoated metal oxides.

25. The composition according to claim 24, wherein the metal oxides are nanopigments chosen from titanium oxide, iron oxide, zinc oxide, zirconium oxide and cerium oxide.

26. The composition according to claim 1, wherein the at least one agent for screening out UV radiation is present in proportions ranging from 0.1% to 20% by weight relative to the total weight of the composition.

27. The composition according to claim 26, wherein the at least one agent for screening out UV radiation is present in proportions ranging from 0.2% to 15% by weight relative to the total weight of the composition.

28. The composition according to claim 1, further comprising at least 5% by weight, relative to the weight of the composition, of at least one polyhydroxylated solvent.

29. The composition according to claim 28, wherein the at least one polyhydroxylated solvent is chosen from glycols and glycol ethers.

30. The composition according to claim 29, wherein the at least one polyhydroxylated solvent is chosen from ethylene glycol, propylene glycol, butylene glycol, dipropylene glycol and diethylene glycol.

31. The composition according to claim 30, wherein the at least one polyhydroxylated solvent comprises a mixture of three different polyhydroxylated solvents.

32. The composition according to claim 31, wherein said mixture comprises propylene glycol, butylene glycol and dipropylene glycol.

33. A cosmetic and/or dermatological composition intended for giving the skin an artificial coloration comprising,
    at least one agent chosen from organic and mineral agents for screening out ultraviolet radiation, and
    at least one flavylium salt compound which is unsubstituted in position 3 and which is substituted with at least one radical chosen from hydroxyl and alkoxy radicals.

34. The composition according to claim 33, wherein the artificial coloration is close to that of a natural tan.

35. A cosmetic and/or dermatological composition intended for giving the skin an artificial coloration comprising,
    at least one agent chosen from organic and mineral agents for screening out ultraviolet radiation, and
    at least one flavylium salt compound which is unsubstituted in position 3 and which is substituted with at least one radical chosen from hydroxyl and alkoxy radicals;
    wherein the at least one flavylium salt compound is obtained in a manner chosen from synthetically, from a plant extract, and from an enriched plant extract containing it.

36. A cosmetic and/or dermatological composition for giving the skin an artificial coloration comprising,
    at least one agent chosen from organic and mineral agents for screening out ultraviolet radiation, and
    at least one flavylium salt compound which is unsubstituted in position 3 and which is substituted with at least one radical chosen from hydroxyl and alkoxy radicals;
    wherein the at least one flavylium salt compound is obtained in a manner chosen from synthetically, from a plant extract, and from an enriched plant extract containing it.

37. A cosmetic treatment process for giving skin an artificial coloration comprising,
applying to the skin in an amount effective for producing said artificial coloration a composition comprising,
at least one agent chosen from organic and mineral agents for screening out ultraviolet radiation, and
at least one flavylium salt compound which is unsubstituted in position 3 and which is substituted with at least one radical chosen from hydroxyl and alkoxy radicals.

38. The process according to claim 37, wherein the at least one flavylium salt compound is obtained in a manner chosen from synthetically, from a plant extract containing it, and from an enriched plant extract containing it.

39. The process according to claim 37, wherein the artificial coloration is close to that of a natural tan.

40. The process according to claim 37, wherein the at least one flavylium salt compound corresponds to formula (I) below:

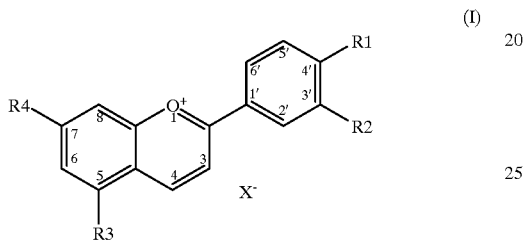

wherein:
$R_1$ is chosen from an OH radical and linear and branched, saturated and unsaturated ($C_1$–$C_8$) alkoxy radicals,
$R_2$, $R_3$ and $R_4$, which may be identical or different, are chosen from H and $R_1$, it being understood that at least one of the radicals $R_1$ to $R_4$ is an OH radical,
$X^-$ is chosen from organic anions and a mineral anions.

41. A method of making a cosmetic and/or dermatological composition with the aim of giving skin an artificial coloration comprising, combining
at least one agent chosen from organic and mineral agents for screening out ultraviolet radiation, and
at least one flavylium salt compound which is unsubstituted in position 3 and which is substituted with at least one radical chosen from hydroxyl and alkoxy radicals.

42. The method according to claim 41, wherein the at least one flavylium salt compound is obtained in a manner chosen from synthetically, from a plant extract containing it, and from an enriched plant extract containing it.

43. The method according to claim 41, wherein the artificial coloration is close to that of a natural tan.

44. The method according to claim 41, wherein the at least one flavylium salt compound corresponds to formula (I) below:

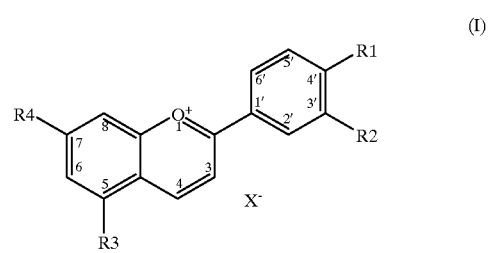

wherein:
$R_1$ is chosen from an OH radical and linear and branched, saturated and unsaturated ($C_1$–$C_8$) alkoxy radicals,
$R_2$, $R_3$ and $R_4$, which may be identical or different, are chosen from H and $R_1$, it being understood that at least one of the radicals $R_1$ to $R_4$ is an OH radical,
$X^-$ is chosen from organic anions and a mineral anions.

* * * * *

UNITED STATES PATENT AND TRADEMARK OFFICE
CERTIFICATE OF CORRECTION

PATENT NO.    : 6,471,949 B2                                          Page 1 of 1
DATED         : October 29, 2002
INVENTOR(S)   : Didier Candau et al.

It is certified that error appears in the above-identified patent and that said Letters Patent is hereby corrected as shown below:

<u>Column 12,</u>
Line 52, after "anions and" delete "a".

<u>Column 13,</u>
Line 52, "thyihexyl" should read -- Ethylhexyl --.

<u>Column 15,</u>
Line 36, after "anions and" delete "a".

<u>Column 16,</u>
Line 37, after "anions and" delete "a".

Signed and Sealed this

Eighteenth Day of March, 2003

JAMES E. ROGAN
*Director of the United States Patent and Trademark Office*